US006334854B1

United States Patent
Davis

(10) Patent No.: US 6,334,854 B1
(45) Date of Patent: Jan. 1, 2002

(54) DYNAMIC RESPONSE ANKLE-FOOT ORTHOSIS

(76) Inventor: Locke Henderson Davis, 3815 Walden Wood La., Chattanooga, TN (US) 37377

( * ) Notice: Subject to any disclaimer, the term of this patent is extended or adjusted under 35 U.S.C. 154(b) by 0 days.

(21) Appl. No.: 09/405,074

(22) Filed: Sep. 27, 1999

(51) Int. Cl.[7] .............................. A61F 5/00; A61F 13/00; B29C 33/40; B29C 47/00
(52) U.S. Cl. ................................. 602/6; 602/27; 602/65; 264/223; 156/245; 156/307.3
(58) Field of Search ................. 602/5–8, 23, 27–29, 602/65; 128/882, 846; 264/222, 223, DIG. 30; 36/140; 12/142 N, 146 M; 156/245, 307.3; 428/36.1, 36.2; 442/260, 261, 263, 305, 318

(56) References Cited

U.S. PATENT DOCUMENTS

| | | | | |
|---|---|---|---|---|
| 3,301,252 A | * | 1/1967 | Mahoney, Jr. | 602/8 |
| 4,286,586 A | * | 9/1981 | Potts | 602/7 |
| 4,289,122 A | * | 9/1981 | Mason | 602/27 |
| 5,154,690 A | * | 10/1992 | Shiono | 602/5 |
| 5,312,669 A | * | 5/1994 | Bedard | 428/105 |
| 5,409,448 A | * | 4/1995 | Kelley | 602/8 X |
| 5,577,999 A | * | 11/1996 | Sekine | 602/6 X |
| 5,817,041 A | * | 10/1998 | Bader | 602/23 |
| 5,833,640 A | * | 11/1998 | Vazquez | 602/27 |
| 6,146,344 A | * | 11/2000 | Bader | 602/5 X |
| 6,146,349 A | * | 11/2000 | Rothschild | 602/5 X |

\* cited by examiner

*Primary Examiner*—Denise Pothier
(74) *Attorney, Agent, or Firm*—Douglas T. Johnson; Stephen J. Stark; Miller & Martin LLP

(57) ABSTRACT

An orthotic device developed and customized to control the desired movement of the patient's defective lower limb. The device incorporates a footplate made of a rubber-like elastomeric material and a proximal segment that encompasses the foot at the metatarsophalangeal joints and the shin portion of the leg. This proximal segment is made of a rubber-like elastomeric material laminated into multiple layers of fabric throughout the proximal segment. Additional strips of fabric are positioned within the proximal segment of the device to limit or promote certain motions within the foot and ankle. This device incorporates a continuous closure from the foot to the proximal segment, creating total contact and hydrostatic containment of the foot and lower leg. The combination of total contact, hydrostatic compression, the multiple layers of fabric with strategically placed strips of fabric laminated with the elastomeric material and the molded footplate combine to provide limited and graded motion of the foot and ankle complex during the gait cycle of ambulation. Much like taping the foot and ankle, this device applies tensile forces to the foot and ankle to control motion. This system applies dynamic corrective forces to the foot and ankle complex during different events of the gait cycle to promote a more normal gait pattern.

3 Claims, 4 Drawing Sheets

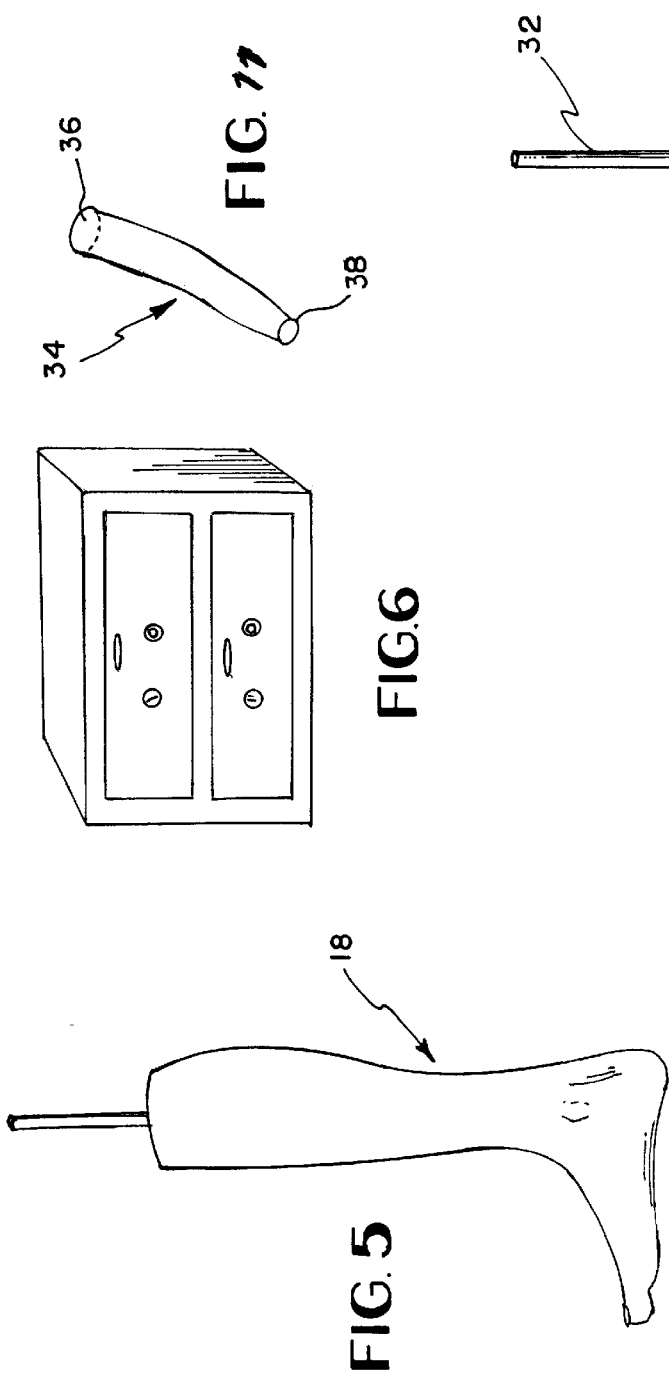

DYNAMIC RESPONSE ANKLE-FOOT ORTHOSIS

BACKGROUND OF THE INVENTION

Ankle foot orthosis are commonly used as foot, ankle, and leg braces for improving movement. Years ago a leg brace would consist of two metal bars and a stirrup attached to the sole of the shoe. A horizontally positioned padded, metal band, contoured to the back of the leg calf, would connect the two metal bars. A broad strap across the anterior section of the calf would hold the brace in place. This type of brace has limited use today, but is not considered to be state of the art orthotic management. This type of device lacks biomechanical control of the foot and ankle and is cumbersome and heavy.

A modern ankle foot orthosis, being a device that applies biomechanical forces to a body segment, is usually fabricated from thermoplastics. The thermoplastic is heat molded over a positive mold similar in shape to the patient's limb, then cooled, and trimmed. Often the thermoplastic is formed into rigid or semirigid laminates. Ankle joint motion in the orthotic device is often provided by a mechanical hinge type joint at the ankle joint.

An existing fundamental problem of orthotic management is that a rigid orthosis, which does not allow plantar flexion of the ankle, will also prevent extension of the hip and knee and causes instability in the hip and knee. Balance at the foot-ankle complex cannot develop because activity and sensation of movement is limited, with resultant muscle wasting.

Current orthotic technology does not allow triplanar activity of the foot and ankle in stance phase found in normal gait. The use of very thin or more flexible plastics has been attempted to allow more motion in the foot and ankle. Much of the benefit of wearing an orthosis is lost when using very flexible plastics, however, in cases where significant control is needed for spastic muscle activity or pathomechanical deformities. The very flexible plastics reduce stability to allow mobility. Allowing motion is not the same as promoting and controlling more normal motion. The disclosure of the present invention promotes and controls more normal motion.

For many patients who require the use of an ankle-foot orthosis, current orthotic technology does not adequately address the dynamic changes that occur in the foot and ankle complex during the gait cycle. Triplanar motion of the foot and ankle requires a dynamic response. Current technology either positions the segments of the foot in a static position or allows motions to occur by reducing the corrective forces. The use of a mechanical ankle joint may provide motion of the talocrural joint in the sagittal plane, however complex motions required within the foot, are restricted from a normal biomechanical response because of the static forces applied by the brace. Optimal orthotic management should control abnormal motion by restricting specific motion during specific events of the gait cycle. This cannot be achieved by holding the segments of the foot in an uniform position throughout the gait cycle. The foot must remain a mobile entity that engages in the normal activity of gait, but is prevented from abnormal motion. Because the needs of the corrective forces of the foot and ankle complex differ within different events of the gait cycle, the ankle-foot orthosis should be dynamic in its application of corrective forces.

Through a dynamic orthosis, a more normal gait pattern can be obtained with less compensatory activity required by proximal segments of the body. The present invention, with its pliable dynamically responding ankle-foot orthosis, provides predetermined corrective forces on the foot and ankle complex during different events of the gait cycle.

SUMMARY OF THE INVENTION

The purpose of this invention is to provide an improved method of controlling the movement of a patient's defective lower limb. The method provides an improved system of constructing a customized ankle-foot orthosis. A combination of physical therapy assessment and orthotic evaluation is utilized to determine design characteristics of the orthosis needed for controlling and improving movement of the defective lower limb movement.

Various other features of the method of the present invention will become obvious to those skilled in the art upon reading the disclosure.

BRIEF DESCRIPTION OF DRAWINGS

Referring now to the drawings, the system is illustrated in views of various stages of construction:

FIG. 5 is a side view of the lower limb mold after removal of the plaster cast;

FIG. 6 is a perspective view of an oven used for heat curing;

FIG. 7 is a perspective view of a roll of KEVLAR or aramid strip material;

FIG. 8 is a perspective view of a container of elastomeric resin;

FIG. 9 is a perspective view of a container of nylon stockinette material;

FIG. 10 is a perspective view of a vacuum attachment;

FIG. 11 is a perspective view of a PVA or polyvinyl alcohol sleeve;

DETAILED DESCRIPTION

Figure 1:
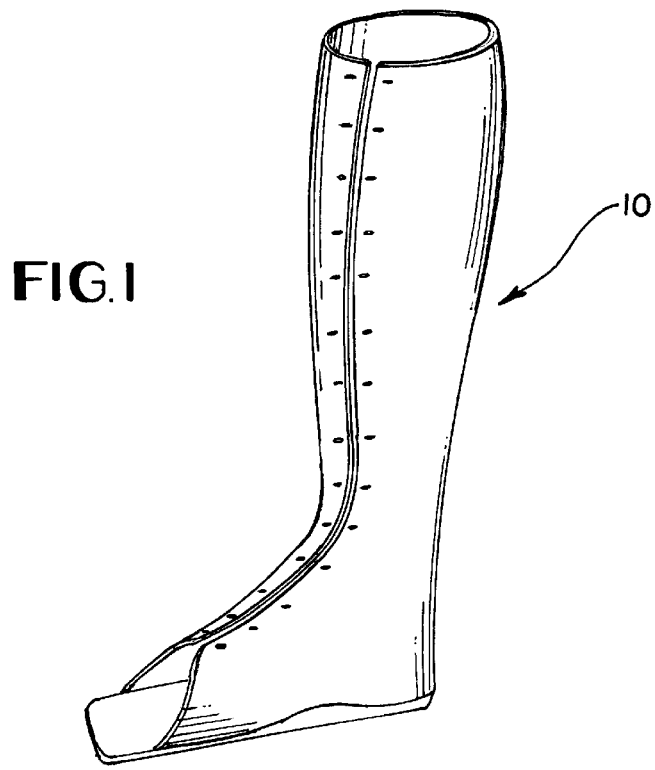
FIG. 1 is a perspective view of the device used to control lower limb movement.

Referring now to FIG. 1, there is illustrated an isometric view of a lightweight and highly flexible orthosis 10 custom built to fit a patient, and used to contain and control the movement of the patient's defective lower limb. The method of control calls for an orthotic evaluation of the patient's lower limb, to determine the needed adjustment and control for the patient's walk and lower limb movement. Based on the evaluation, a mold of the patient's lower limb is used to produce a laminated device providing the desired control and to improve movement of the defective lower limb.

Figure 2:
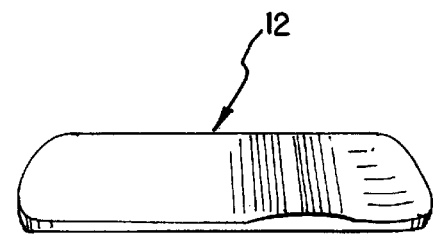
FIG. 2 is a perspective view of a contoured footplate used for lower limb support.
Figure 3:
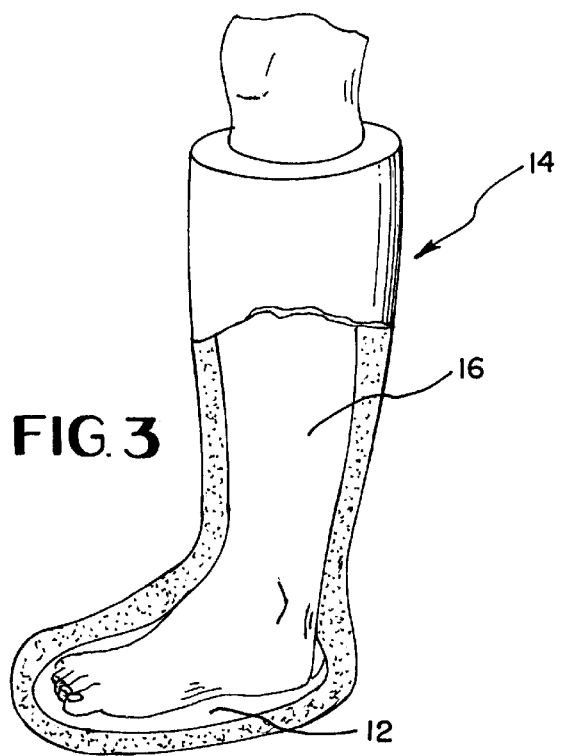
FIG. 3 is a cut-a-way view of the lower limb positioned in a plaster cast.
Figure 4:
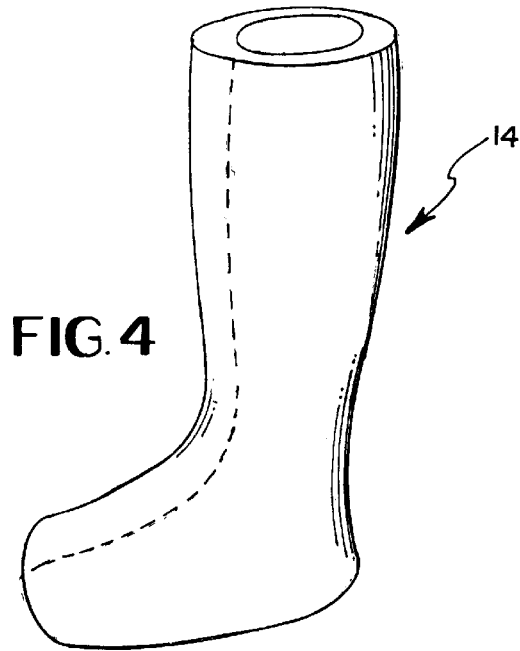
FIG. 4 is a perspective view of the plaster cast with the lower limb removed and positioned to receive molding plaster.

A footplate 12, shown in FIG. 2 preferably developed from a rubber-like elastomeric material, is designed and contoured to fit and support the plantar surface of the patient's foot. A plaster cast 14, shown in cut-a-way view in FIG. 3, is then made of the patient's lower limb 16 up to the fibula head with the foot positioned on the footplate 12 in a fixed orthotically designed position. After sufficient hardening, the patient's lower limb 16 is removed by making a cutline, leaving the plaster cast 14, shown in FIG. 4, with the footplate 12 remaining in the cast. The cast is sealed along the cut line, and the cast 14 may then be filled with molding plaster to create a mold of the patient's lower limb. The footplate 12 correctly shapes the plantar foot surface of the mold.

Figure 12:
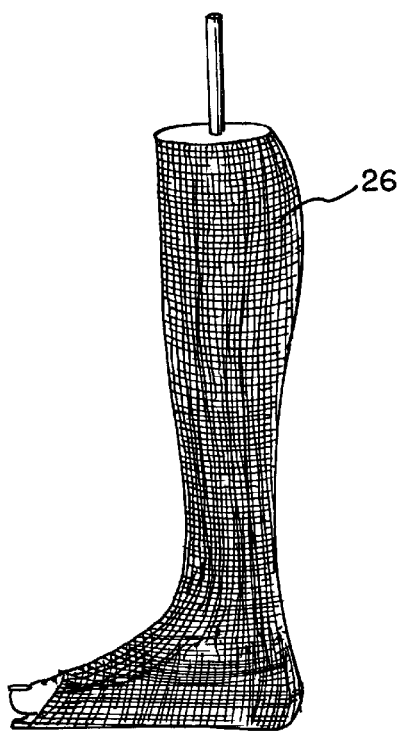
FIG. 12 is a side perspective view of layers of nylon stockinette positioned over the lower limb mold.

After the mold has hardened sufficiently, the outer cast 14, with the footplate 12, is removed and any adjustment of the mold's surface can be corrected by applying or removing needed plaster and by smoothing the surface of the mold, thus creating a plastermold 18 of the patient's lower limb, shown in FIG. 5. To insure proper curing, the mold 18 is allowed drying time in a low temperature oven, as shown in FIG. 6. The lower limb plaster mold 18 is the treated by saturating its entire surface with a rubber-like elastomeric resin 20, shown in FIG. 8, over which at least two layers of nylon stockinette 22 are applied, as shown in FIGS. 9 and 12.

Figure 13:
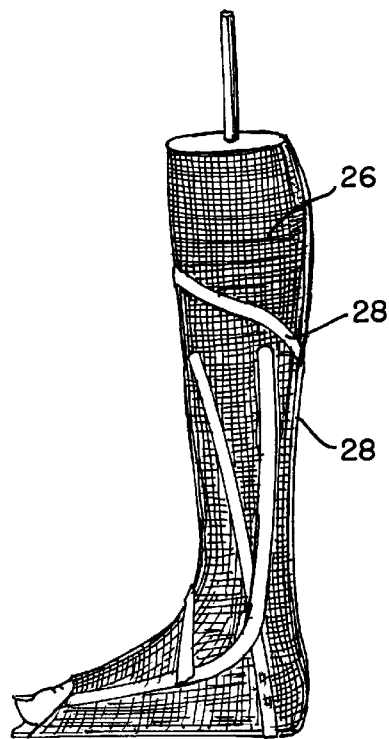
FIG. 13 is a perspective view of aramid strips strategically positioned in various patterns over the stockinette material.

Strips 28 made of KEVLAR™ or aramid fabric 24 shown in FIG. 7, of selected width and with light adhesive, are attached in specific selected patterns to the set-ups stockinette surface 26 as shown in FIG. 13 to create and control predetermined lower limb movement patterns, as determined by the orthotic evaluation. By adjusting the arrangements of the strips 28, desired alterations in leg and foot movement are achieved with a light, pliable and highly flexible orthosis.

Figure 14:
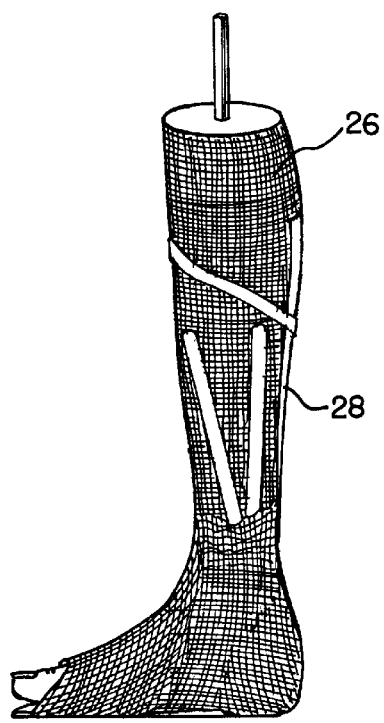
FIG. 14 is a side perspective cutaway view of additional layers of stockinette material positioned over the strips and underlying stockinette material.

At least one more layer of stockinette material 22 is applied over the strips 28 of the set-up, as shown in cut-a-way view of FIG. 14. The laminate set-up is then positioned onto a vacuum stand 32, shown in FIG. 10, and covered with a dampened PVA (polyvinyl alcohol) sleeve 34, shown in FIG. 11, having its upper end 36 closed and its lower end 38 sealed to the vacuum stand 32, thus allowing a sufficient vacuum to occur between the outer surface of the set-up and the PVA sleeve 34, to enhance drying.

Figure 15:
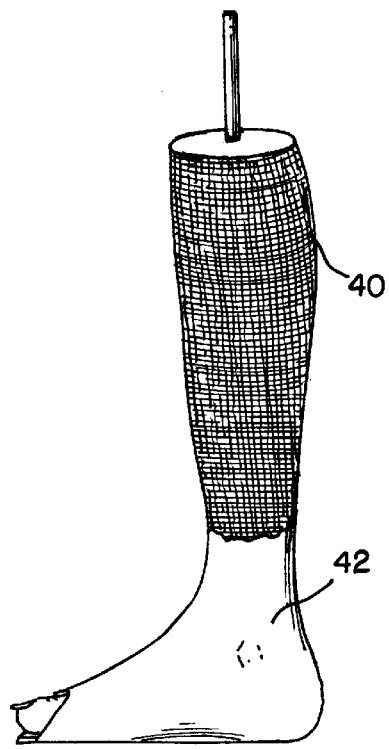
FIG. 15 is a cut-a-way view of the outside application of the elastomeric resin.

The upper end 36 of the PVA sleeve 34 is then opened and elastomeric resin is uniformly applied to the stockinette fabric set-up 40 visible in the cut-a-way view of FIG. 15. FIG. 15 illustrates the stockinette fabric set-up along the calf portion in the cut-away portion and the outer finish 42 of the applied elastomeric resin, as applied uniformly. The stockinette fabric set up 40 and outer finish 42 are vacuum dried along the foot portion. After completing the resin application uniformly, the upper end 36 of the PVA sleeve 34 is re-closed to allow set-up-drying time under vacuum, then heat-cured for a sufficient time under selected heat and cooled to room temperature. Any excess elastomeric resin is removed from the toe section of the set-up. The laminated set-up is then soaked in hot water and the PVA is washed from the lamination.

Figure 17:
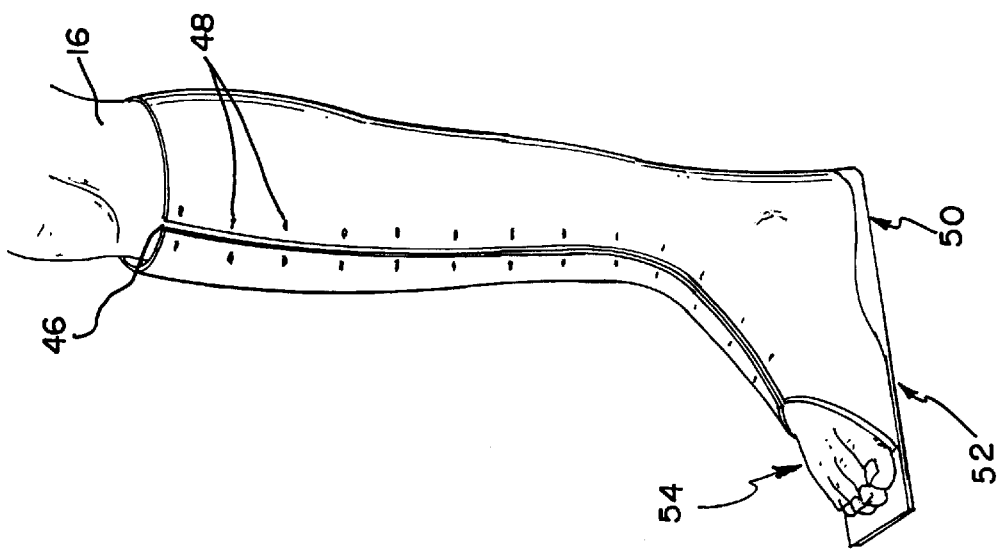
FIG. 17 is a perspective view of the laminated orthosis fitted on the patient's lower limb and in a position for lacing or closing.
Figure 16:
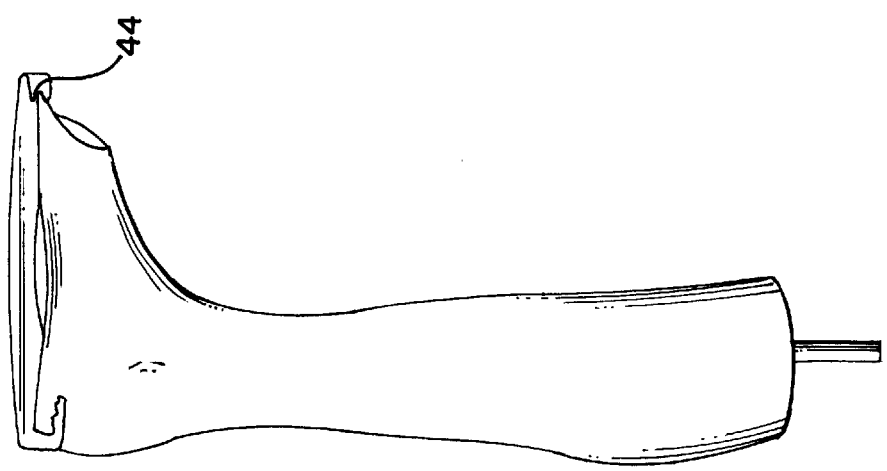
FIG. 16 is side view of the laminated mold set-up in an inverted position for building up the plantar surface.

After drying, the laminated set-up's plantar surface of the foot section is sanded until the fibers of the nylon stockinette are exposed. The set-up is then positioned in an inverted position with the plantar foot section in a horizontal position in the sagittal and frontal plane, as shown in FIG. 16. A dam is built of selected height, around the border of the foot with masking tape 44, see cut-a-way view of FIG. 16. The plantar surface is then filled to the selected depth with elastomeric resin, allowed sufficient curing time, and then heat cured. The masking tape 44 is removed and excessive material is sanded away. A center dividing line is cut down the front of the laminated set-up device, the mold is then removed and the laminated set up is selectively trimmed. Continuous closing means 48 are constructed in series down each side of the laminated set-up anterior opening 46. FIG. 17 illustrates the orthosis apparatus 10 containing the patient's lower limb 16, and positioned to receive lacing or other means of continuous closing, thus establishing a method of controlling the movement of a patient's lower limb 16.

In practice, a patient with a defective lower limb 16 is evaluated by an orthotic doctor who determines the corrective movements that are needed to benefit the patient's walk and lower limb movement. To implement the beneficial collective movement a light and flexible lower limb encasement or boot is constructed that only permits movement that coincides with the beneficial pattern. To create and construct this encasement, or orthosis 10, it is desirable to make a plaster mold 18, duplicating the patient's lower limb.

The lower limb mold 18 is covered, until saturated, over its entire outer surface with a rubber-like elastomeric resin and at least two layers 26 of nylon stockinette 22 are applied, as shown in FIG. 12. Aramid fiber strips 28 of selected width and with light adhesive are applied to the stockinette 26 in specific predetermined patterns as shown in FIG. 13 that only allow selected movements of the patients lower limb 16. At least two additional layers of stockinette material 22 are applied over the existing set-up and its strips 28, as visible in the cut-a-way view of FIG. 14. The mold, being inverted onto a vacuum stand 32, is covered with a dampened PVA sleeve 34 and positioned for a sufficient vacuum between the mold surface and the PVA sleeve 34 to dry the rubber-like elastomeric resin applied uniformly over the fabric set-up. After curing and low oven drying, the PVA sleeve is washed from the laminated set-up and the set-up is placed in an inverted position, with the foot horizontal, to allow the construction of a dam made with masking tape 44 around the foot border, so that elastomeric resin can be applied to the foot plantar surface. After heat curing and removing the masking tape 44, excessive material is sanded away. A center dividing line is cut down the front of the laminated set-up and the setup is removed from the mold 18. Surplus lamination material is trimmed away at the toe section 54 and closing means 48 are constructed in series on each side of the anterior opening 46. In this fashion, an orthosis 10 is created for controlling the movement of the patient's defective lower limb 16.

It is to be understood that the foregoing drawings and description of the invention is to be taken as a preferred embodiment and that various other modifications will occur to those skilled in the art upon reading the disclosure, however all changes and modifications that come within the spirit of the invention are desired to be protected.

I claim:

1. A method of controlling the movement of a defective lower limb of a patient, comprising the steps of:
   a) having a person with specific corrective needs in the movement of a lower limb;
   b) evaluating and determining by an orthotic examination design characteristics needed to improve movement of the defective lower limb;

c) constructing a specifically designed plaster mold that is a duplicate of the defective lower limb;

d) coating the mold with an elastomeric resin for constructing over the mold a laminated set-up for lower limb motion control;

e) applying at least two layers of nylon stockinette over the mold;

f) attaching aramid fiber strips, being of selected width, in specific patterns onto the layers of nylon stockinette, and strategically placed on the layers of nylon stockinette to coincide with the lower limb movement needs previously determined by the orthotic evaluation;

g) applying at least two additional layers of nylon stockinette over the aramid fiber strips forming the laminated set-up;

h) inverting the laminated set-up onto a vacuum stand;

i) covering the laminated set-up with a dampened poly vinyl alcohol sleeve, having an upper end closed and sealing a lower end to the vacuum stand, thus allowing a sufficient vacuum to occur between the surface of the mold and the poly vinyl alcohol sleeve, for drying purposes;

j) opening the upper end of the poly vinyl alcohol sleeve and applying uniformly to the laminated set-up, an elastomeric resin that produces a coating;

k) re-closing the upper end of the poly vinyl alcohol sleeve and allowing the laminated set-up time for drying under vacuum, l) heat-curing the laminated set-up for a sufficient time under sufficient heat;

m) cooling the laminated set-up to room temperature and removing any excess elastomeric resin from a toe section of the laminated set-up;

n) soaking the laminated set-up in hot water and washing the poly vinyl alcohol from the laminated set-up;

o) drying the laminated set-up and sanding a plantar surface of a foot section of the laminated set-up until fibers of the nylon stockinette layers are exposed;

p) positioning the laminated set-up in an inverted position with the foot section horizontal in the sagittal and frontal plane;

q) building a dam of selected height around a border of the foot section with masking tape;

r) filling the plantar surface with elastomeric resin and allowing it sufficient time to cure;

s) heating the laminated set-up for a sufficient time, for curing purposes;

t) removing the masking tape and, sanding away excess material, u) cutting a center dividing line down the front of the laminated set-up and trimming away the lamination exposing a toe area section;

v) constructing closing means;

w) removing the laminated set-up from the mold to provide a pliable orthosis for controlling the motion of the defective lower limb; and x) placing the defective lower limb of the patient inside the orthosis with the closing means whereby the specifically placed strips of the orthosis control the defective lower limb movement in accordance with the previously determined orthotic design characteristics.

2. A method of controlling the movement of a defective lower limb of a patient, comprising the steps of a) orthotically evaluating a person with specific corrective needs in the movement of a defective lower limb;

b) determining design characteristics needed to improve the defective lower limb movement;

c) designing and fabricating a contoured footplate, for supporting a desired lower limb position;

d) positioning the footplate beneath a foot of the lower limb in contact with the plantar surface of the foot;

e) incorporating the footplate, foot and lower leg into a plaster cast, encompassing the entire foot and leg up to the fibula head and holding in a fixed orthotically desired position;

f) after sufficient hardening, making a cut line and removing the cast and the footplate from the foot and leg;

g) sealing the cast along the cut line;

h) filling the cast with molding plaster creating a mold of the defective lower limb;

i) removing the cast with the footplate from the hardened plaster mold and correcting any needed adjustment to the mold with regards to the foot and ankle;

j) adjusting a surface of the plaster mold as needed to desired contours by applying and removing plaster and by smoothing the surface of the molds, thus creating the mold of the patient's lower limb;

k) drying the mold in a low temperature oven;

l) coating the entire mold with an elastomeric resin for constructing over the mold a laminated set-up for lower limb motion control;

m) applying at least two layers of nylon stockinette over the mold;

n) attaching aramid fiber strips of selected width and having light adhesive in specific patterns onto the nylon stockinette layers, and strategically placed on the nylon stockinette layers to improve the defective lower limb movement as previously established by the orthotic evaluation;

o) applying at least two additional layers of nylon stockinette over the aramid fiber strips forming the laminated set-up;

p) inverting the laminated set-up onto a vacuum stand;

q) covering the laminated set-up with a dampened poly vinyl alcohol sleeve having an upper end closed and sealing a lower end to the vacuum stand thus achieving a sufficient vacuum between the surface of the laminated set-up and the poly vinyl alcohol sleeve for drying purposes;

r) opening the upper end of the poly vinyl alcohol sleeve and applying uniformly to the laminated set-up, an elastomeric resin that produces a coating;

s) re-closing the upper end of the poly vinyl alcohol sleeve and allowing the laminated set-up drying time under vacuum;

t) heat-curing the laminated set-up for a sufficient time and under sufficient heat;

u) cooling the laminated device to room temperature and removing any excess elastomeric resin from a toe section of the laminated set-up;

v) soaking the set-up device in hot water and washing the poly vinyl alcohol from the laminated set up;

w) drying the laminated set-up device and sanding a plantar surface of a foot section of the laminated set-up until fibers of the nylon stockinette are exposed;

x) positioning the laminated set-up in an inverted position with the foot section horizontal in the sagittal and frontal plane;

y) building a dam, of selected height, around a border of the foot section, with masking tape;

z) filling the plantar surface with elastomeric resin and allowing it sufficient time to cure;

aa) heating the laminated set-up for a sufficient time, for curing purposes;

bb) removing the masking tape and sanding away excess material, cc) cutting a center dividing line down the front of the laminated set-up and trimming away lamination to expose a toe area section;

dd) constructing closing means;

ee) removing the laminated set-up from the mold to provide an orthosis for controlling the motion of the lower limb; and p1 ff) placing the defective lower limb inside the orthosis, and with the closing means controlling the lower limb movement of the patient to coincide with predetermined orthotic requirements for triplane movement.

3. A method of controlling the movement of a defective lower limb of a patient with an orthosis comprising the steps of:

(a) evaluating specific corrective needs in the movement of a lower limb;

(b) constructing a mold of the defective lower limb;

(c) applying at least one fabric layer over the mold;

(d) attaching at least one aramid strip to control movement of the orthosis to coincide with desired lower limb movement established by the orthotic evaluation;

(e) applying at least two additional layers of fabric over the at least one aramid strip;

(f) applying a dampened poly vinyl alcohol sleeve over the fabric covered mold;

(g) applying elastomeric resin to produce a laminate into the fabric layers;

(h) curing the resin;

(i) sanding a plantar surface of the laminate until one of the fabric layers is exposed;

(j) building a dam around the border of a foot section of the laminate;

(k) filling the plantar surface of the foot section within the dam with a thickness of elastomeric resin;

(l) curing the resin;

(m) removing the orthosis from the mold; and (n) placing the orthosis over the defective lower limb of the patient to control limb movement.

* * * * *